US012502301B2

(12) United States Patent
Liu et al.

(10) Patent No.: US 12,502,301 B2
(45) Date of Patent: Dec. 23, 2025

(54) FINGER TENDON SHEATH BRACE CAPABLE OF ADJUSTING FIXING PRESSURE AND KIT THEREOF

(71) Applicant: Shanghai Sixth People's Hospital, Shanghai (CN)

(72) Inventors: Shen Liu, Shanghai (CN); Xuanzhe Liu, Shanghai (CN); Weiguang Yin, Shanghai (CN); Cunyi Fan, Shanghai (CN); Wei Wang, Shanghai (CN)

(73) Assignee: Shanghai Sixth People's Hospital, Shanghai (CN)

(*) Notice: Subject to any disclaimer, the term of this patent is extended or adjusted under 35 U.S.C. 154(b) by 167 days.

(21) Appl. No.: 18/410,251

(22) Filed: Jan. 11, 2024

(65) Prior Publication Data

US 2024/0139018 A1 May 2, 2024

Related U.S. Application Data

(63) Continuation of application No. PCT/CN2022/136515, filed on Dec. 5, 2022.

(30) Foreign Application Priority Data

Aug. 18, 2022 (CN) ......................... 202210995398.1

(51) Int. Cl.
*A61F 5/058* (2006.01)

(52) U.S. Cl.
CPC ................................ *A61F 5/05875* (2013.01)

(58) Field of Classification Search
CPC ........ A61F 5/05875; A61F 5/05; A61F 5/058; A61F 5/04; A61F 5/01; A61F 5/00; A61F 5/042; A61B 17/22
See application file for complete search history.

(56) References Cited

U.S. PATENT DOCUMENTS

2021/0338514 A1 11/2021 De La Torre Barreiro
2022/0023029 A1 1/2022 Moradi et al.
2022/0401299 A1* 12/2022 Tsai ...................... G16H 20/90

FOREIGN PATENT DOCUMENTS

CN 1422601 A * 6/2003
CN 207545735 U 6/2018
(Continued)

OTHER PUBLICATIONS

International Search Report for PCT/CN2022/136515, mailed Mar. 22, 2023.

*Primary Examiner* — Tarla R Patel
(74) *Attorney, Agent, or Firm* — Pilloff Passino & Cosenza LLP; Rachel K. Pilloff; Sean A. Passino

(57) ABSTRACT

Provided is a finger tendon sheath brace capable of adjusting fixing pressure, including a brace fixing plate, a compression screw, a compression plate, an adjustable pressure push rod and a spring. The brace fixing plate is configured as a fixing structure for accommodating a finger to extend in the finger tendon sheath brace, and is provided with a threaded opening in a center of the brace fixing plate in a vertical direction perpendicular to the finger. The compression screw is embedded in the threaded opening of the brace fixing plate through threads to make an end of the compression screw slightly higher than the brace fixing plate and a head end of the compression screw pass through the brace fixing plate and enter a cavity for accommodating the finger. The compression plate is connected with a head end of an adjustable pressure push rod inner sleeve.

8 Claims, 5 Drawing Sheets

(56) References Cited

FOREIGN PATENT DOCUMENTS

| | | | | | |
|---|---|---|---|---|---|
| CN | 110680589 A | * | 1/2020 | ............... | A61F 5/05 |
| CN | 112155655 A | | 1/2021 | | |
| CN | 112869951 A | | 6/2021 | | |
| CN | 112998810 A | * | 6/2021 | ............. | A61B 17/12 |
| CN | 215273416 U | * | 12/2021 | | |
| CN | 112998810 B | * | 11/2022 | ............. | A61B 17/22 |

* cited by examiner

FINGER TENDON SHEATH BRACE CAPABLE OF ADJUSTING FIXING PRESSURE AND KIT THEREOF

CROSS-REFERENCE TO RELATED APPLICATIONS

This application is a continuation of PCT/CN2022/136515, filed Dec. 5, 2022 and claims priority of Chinese Patent Application No. 202210995398.1, filed on Aug. 18, 2022, the contents of which are hereby incorporated by reference.

TECHNICAL FIELD

The application relates to a fixing device of finger tendon sheath, and in particular to a finger tendon sheath brace capable of adjusting fixing pressure and a kit thereof.

BACKGROUND

A finger tendon rupture caused by an injury or a disease is usually difficult to recover and often requires a surgical treatment. Fingers are very nimble and difficult to fix. After conventional plaster fixation, a patient often habitually uses his fingers, thus leading to active contraction of finger muscles and displacement of tendon and tendon sheath. In addition, the displacement of the tendon and the tendon sheath of the fingers may be sometimes caused due to unintentional passive movement.

The tendon sheath may secrete synovial fluid to promote tendon healing, and integrity of the tendon sheath is very important to maintain a shape and a function of the tendon after healing. Therefore, accelerating the healing of the tendon sheath may improve a speed and an effect of recovery. However, in order to accelerate the healing of the tendon sheath, it is necessary to stabilize a position of the tendon sheath and ensure that pressure around the tendon sheath will not be too large. Otherwise, surrounding tissues are compressed, and reflux of blood and lymph is blocked, resulting in local blood circulation disorder. Previous studies have shown that mechanical stress plays a key role in the tendon healing. The pressure around the finger tendon sheath fluctuates between 30 mmHg-100 mmHg, depending on the position of the finger tendon sheath and a posture of a finger. Moreover, pressure in the tendon sheath increases significantly during an active movement, which is not conducive to the tendon healing. Therefore, it is hoped to design a brace that may keep the pressure around tendon constant and simulate a relationship between normal tendon sheath and normal tendon.

According to China patent (CN212015889U, Finger Tendon Sheath Brace), this structure has played a key role in fixing the tendon sheath. However, when used on fingers, this structure is complex, inconvenient to wear, and unable to adjust constant pressure. Therefore, this structure is not conducive to healing of the tendon sheath.

SUMMARY

An objective of this application is to provide a finger tendon sheath brace capable of adjusting fixing pressure for adjusting pressure between a compression plate and skin to maintain surface pressure of surface skin in a stable range. On the one hand, pressure exerted by a compression screw is similar to pressure exerted by tendon on a pulley. On the other hand, local swelling and further skin necrosis caused by compression on a finger is avoided. In addition to a function of adjusting the pressure, a design of this application has better performances of comfort, anti-dropping, anti-rotation and fixing than an original technology.

One aspect of the application discloses a finger tendon sheath brace capable of adjusting fixing pressure, including a brace fixing plate, a compression screw, a compression plate, an adjustable pressure push rod and a spring.

The brace fixing plate is configured as a fixing structure for accommodating a finger to extend in the finger tendon sheath brace, and is provided with a threaded opening in a center of the brace fixing plate in a vertical direction perpendicular to the finger.

The compression screw is embedded in the threaded opening of the brace fixing plate through threads, so that an end of the compression screw is slightly higher than the brace fixing plate, and a head end of the compression screw passes through the brace fixing plate and enters a cavity for accommodating the finger.

The compression plate is connected with a head end of an adjustable pressure push rod inner sleeve.

The spring is arranged in the compression screw and used for adjusting a pressure applied on the compression plate by the compression screw, so as to fix tendon sheath.

In an embodiment, a shape of the brace fixing plate is selected from a group consisting of an O-ring, a rectangular ring, and a C-shaped semi-ring with one side open.

In an embodiment, the compression plate has a narrow strip structure.

In an embodiment, a lower part of the compression screw is connected with a sleeve structure, the sleeve structure has a layered structure with inner and outer layers and comprises the adjustable pressure push rod inner sleeve and an adjustable pressure push rod outer sleeve.

External threads are arranged on the adjustable pressure push rod outer sleeve for matching with a head end of the compression screw.

The adjustable pressure push rod inner sleeve is sleeved inside the adjustable pressure push rod outer sleeve and vertically displaces relative to the adjustable pressure push rod outer sleeve through the spring.

In an embodiment, in the vertical direction, the spring is arranged at an end of the adjustable pressure push rod inner sleeve close to the finger or at an end away from the finger.

In a preferred embodiment, the compression plate is connected with the adjustable pressure push rod inner sleeve.

In an embodiment, a skin-friendly soft sponge is attached to one end of the compression plate in direct contact with the finger, and/or an inner surface of the brace fixing plate is covered with the skin-friendly soft sponge.

In an embodiment, when the spring is located at the end of the adjustable pressure push rod inner sleeve away from the finger, the adjustable pressure push rod outer sleeve is provided with a transparent spring position display window at a corresponding position of the spring, and a spring display bar is marked on the spring and moves up and down in the spring position display window according to a position of the spring. An outer side of the spring position display window is provided with scales indicating pressure values of the spring.

In an embodiment, pressure states inside the finger tendon sheath brace are marked with three scale lines.

When pressure in the finger tendon sheath is greater than 100 mmHg, the spring display bar corresponds to a first scale line in the spring position display window.

When the pressure in the finger tendon sheath is greater than or equal to 40 mmHg and less than 100 mmHg, the spring display bar corresponds to a second scale line in the spring position display window of the tendon sheath brace.

When the pressure in the finger tendon sheath is less than 40 mmHg, the spring display bar corresponds to a third scale line in the spring position display window of the tendon sheath brace.

Another aspect of the application discloses a kit of the finger tendon sheath brace, including a plurality of finger tendon sheath braces as described in any one of the above, and further including link blocks, and retractable anti-dropping strips. The kit is configured to provide tendon sheath fixation for a plurality of finger injuries. The link blocks connect the multiple finger tendon sheath braces in parallel through link rods.

The application at least has following beneficial effects.

1. The brace fixing plate may effectively fix a position of the tendon sheath and accelerate recovery of the tendon sheath.
2. Through a design of an adjustable pressure push rod and the spring, an excessive pressure of the push rod may be effectively avoided, and the pressure in tissue may be avoided from rising, which is not conducive to healing of the tendon sheath and tendon.
3. An outer side of the adjustable push rod is provided with a transparent indicator strip to ensure that skin and soft tissue blood vessels are not compressed due to excessive pressure of the push rod, and to avoid causing limb swelling and skin tissue necrosis.
4. A height of the compression screw may be adjusted by twisting to adapt to thicknesses of different fingers and positions of the tendon sheath.
5. A problem that a conventional brace compression screw affects finger movement is greatly solved through a small elastic notch of the brace and an embedded design of the compression screw at a top.
6. The retractable anti-dropping strip and the compression plate in a narrow strip-shaped "surfboard" type increase abilities of anti-dropping and anti-rotation of the brace.
7. A multiple finger injury link block and a link rod of the brace ensure that the finger may be fixed with the brace at every tendon injury, thus enhancing universality of the brace.
8. The soft sponge lined in an inner side of the brace and the compression plate greatly improves comfort of the brace and avoids pressure sores caused by hard compression.
9. A normal physiological environment of the tendon sheath is simulated, healing and recovery of the tendon sheath and the tendon are accelerated, and the application is easy to use and has a wide range of applications.

A large number of technical features are recorded in the specification of this application, which are distributed in various technical schemes. If all possible combinations of the technical features (technical schemes) of this application are listed, the specification will be too lengthy. In order to avoid this problem, all the technical features disclosed in the above summary of the present application, technical features disclosed in the following embodiments and examples, and technical features disclosed in drawings may be freely combined with each other to form various new technical schemes (all these technical schemes should be regarded as already recorded in this specification), unless combination of such technical features is technically infeasible. For example, in one example, features A+B+C are disclosed, and in another example, features A+B+D+E are disclosed, and a feature C and a feature D are equivalent technical means that have the same effect. Technically, it is only necessary to use one of them, and it is impossible to use them at the same time. A feature E may be combined with the feature C technically, so a scheme of the A+B+C+D should not be regarded as recorded because it is not technically feasible, while a scheme of the A+B+C+D should be regarded as recorded.

DETAILED DESCRIPTION OF THE EMBODIMENTS

In the following description, many technical details are set forth for readers to better understand this application. However, those skilled in the art may understand that even without these technical details and various changes and modifications based on following embodiments, technical schemes claimed in this application may be realized.

Terms

As used herein, "finger tendon sheath brace capable of adjusting fixing pressure", "finger tendon sheath brace", "tendon sheath brace" and "brace" are used interchangeably, and all refer to the finger tendon sheath brace capable of adjusting the fixing pressure in this application.

Some innovations of the embodiments of the present application are briefly described below.

Figure 1:
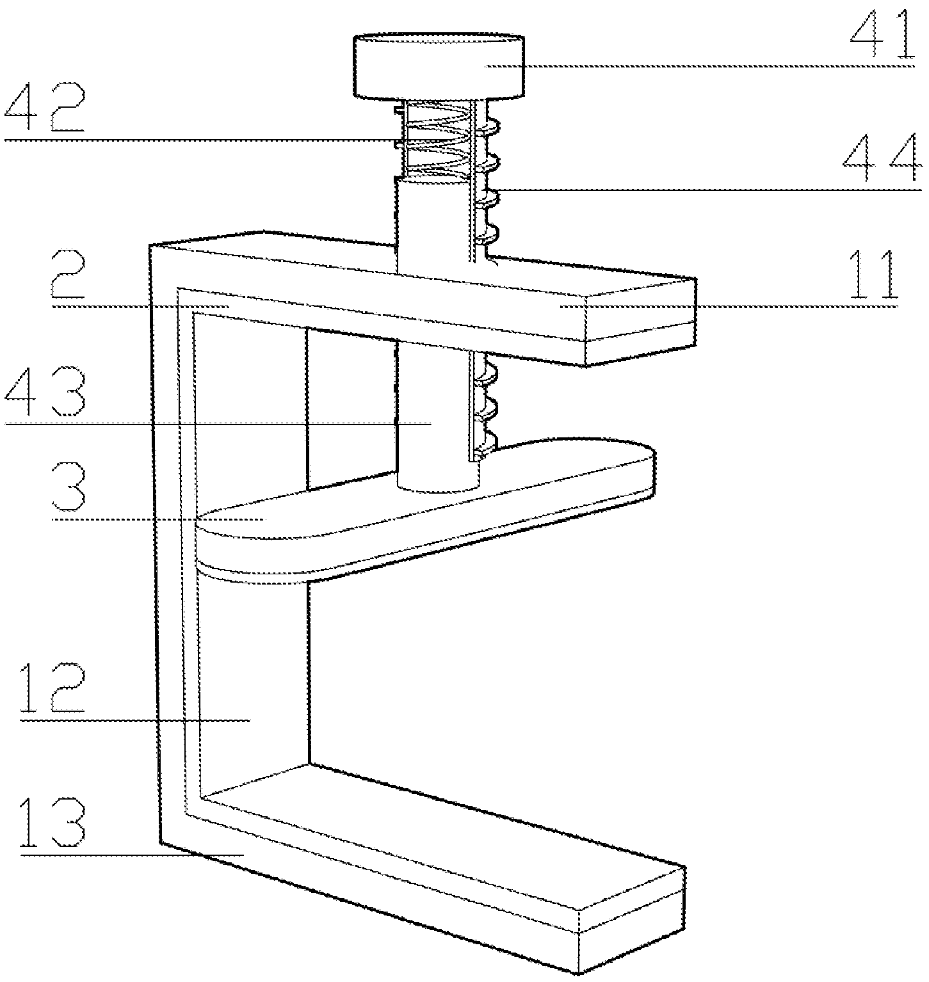
FIG. 1 is a main sectional view of a finger tendon sheath brace capable of adjusting fixing pressure according to an embodiment of the present application.
Figure 4:
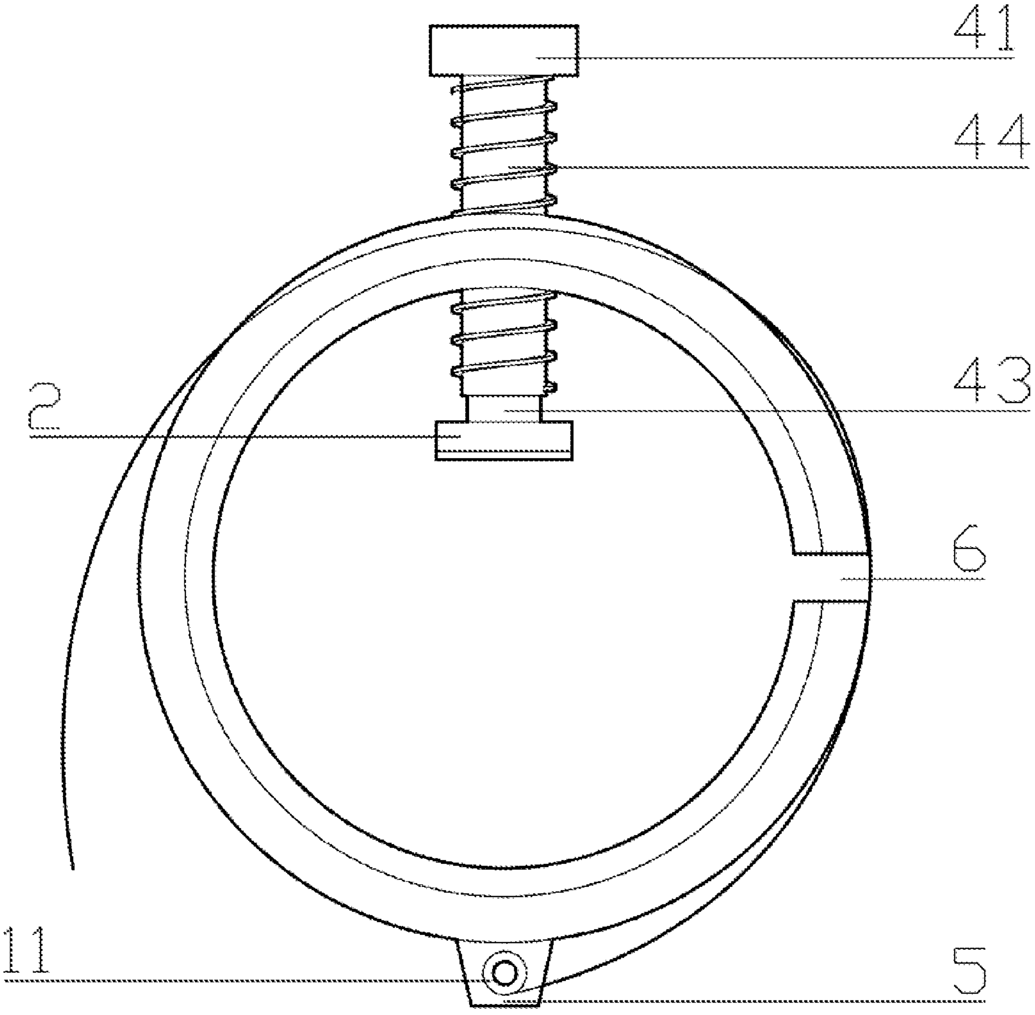
FIG. 4 is a main sectional view of a finger tendon sheath brace capable of adjusting fixing pressure according to another embodiment of the present application.

As shown in FIG. 1, the finger tendon sheath brace capable of adjusting the fixing pressure in the application includes a brace fixing plate 1, a skin-friendly soft sponge 2, a compression plate 3, a compression screw 41, a spring 42, an adjustable pressure push rod inner sleeve 43, an adjustable pressure push rod outer sleeve 44, a spring display bar 45, a spring display window 46 and a spring scale table 47. In an alternative embodiment, as shown in FIG. 4, the brace further includes a multiple finger injury link block 5, an elastic notch 6, a retractable anti-dropping strip 11, and a multiple finger injury link rod 12. The brace fixing plate and the elastic notch 6 form an opening structure for accommodating a finger to enter in. The brace fixing plate is lined with the skin-friendly soft sponge 2 to prevent compression and necrosis of local tissue caused by finger insertion.

A compression structure is a threaded hollow push rod structure, including the compression plate 3, the compression screw 41, the spring 42, the adjustable pressure push rod inner sleeve 43 and the adjustable pressure push rod outer sleeve 44. The compression plate 3 is located in a center of the brace fixing plate, and is lined with the skin-friendly soft sponge 2 below. The compression plate is a narrow strip structure. On the one hand, the compression plate limits a compression range to the tendon sheath, without compressing surrounding blood vessels and nerves. On the other hand, the compression plate is fixed between interphalangeal joints, and is used together with the retractable anti-dropping strip on a back side of the brace to enhance anti-dropping and anti-rotation of the brace and enhance a fixation performance. A head end of the compression screw 41 passes through and extends into a space in the brace, and the adjustable pressure push rod outer sleeve 44 is connected to the compression screw 41 through threads, and the adjustable pressure push rod inner sleeve 43 is sleeved in the outer sleeve, and one end facing the finger is connected with the compression plate 3. The spring 42 is located in the adjustable pressure push rod outer sleeve 44, and may be arranged at a top end of the inner sleeve 43 or at a bottom (i.e., one end close to the finger) of the inner sleeve 43. The spring adjusts pressure between the compression plate and skin more flexibly, so that skin surface pressure is maintained in a stable range. On the one hand, pressure exerted by the compression screw is similar to pressure exerted by tendon on a pulley. On the other hand, local swelling and further skin necrosis caused by compression on the finger is avoided.

Figure 2:
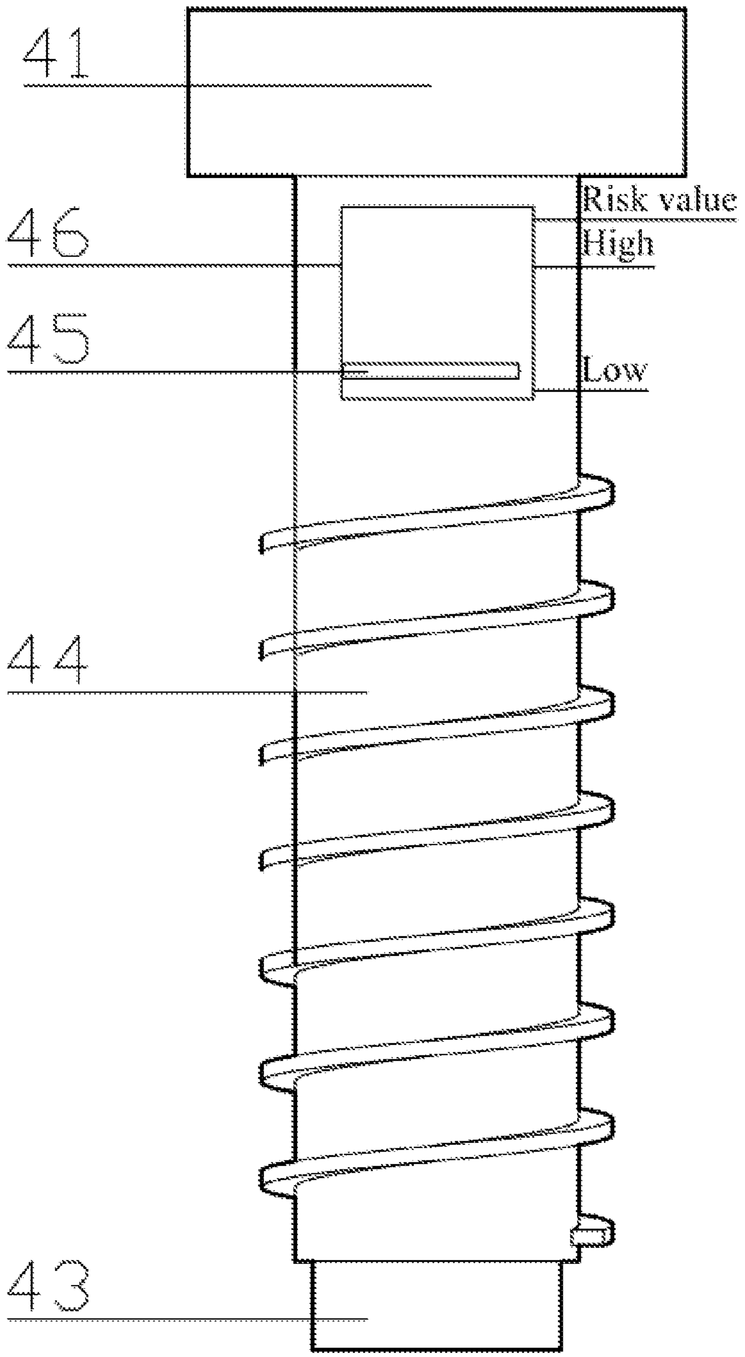
FIG. 2 is a front view of an outer surface of a compression screw according to one embodiment.

As shown in FIG. 2, there is a transparent spring position display window 46 in the adjustable pressure push rod outer sleeve 44 parallel to the spring 42. The spring display bar 45 moves in the window, and scales indicating pressure values of the spring are arranged outside the spring position display window. Pressure states inside the finger tendon sheath brace are marked with three scale lines. When a compression limit of the spring is high, the spring display bar moves to a high position, or when a pressure value is greater than a certain value, the spring display bar corresponds to a first scale line in the spring position display window. When the compression limit of the spring is moderate, the spring display bar moves to a middle position of the display window, or when the pressure value is in a certain range, the spring display bar corresponds to a second scale line in the spring position display window of the tendon sheath brace. When the compression limit of the spring is very small, the spring display bar moves to a lower position, or when the pressure in the finger tendon sheath is less than a certain value, the spring display bar corresponds to a third scale line in the spring position display window of the tendon sheath brace.

In order to make an objective, a technical scheme and advantages of this application clearer, the embodiments of this application will be further described in detail with attached drawings.

Embodiment 1

One embodiment of the present application is shown in FIG. 1 and FIG. 2. A brace fixing plate is in a shape of a C-shaped opening, including an upper arm, a middle arm and a lower arm. The upper arm and the lower arm are connected by a vertical middle arm. An outer sleeve is in threaded connection with a compression screw through threads distributed on the outer sleeve. A spring is located between the outer sleeve and an inner sleeve, and at one end of the inner sleeve away from a finger. The finger is put between a compression plate and a brace fixing plate 1, and a compression screw 41 is tightened to a moderate tightness to complete fixation of finger tendon sheath. It is best to make a spring display bar 45 at a low scale during tightening, so as to allow tendon to slide in the tendon sheath, and meanwhile to avoid that soft tissue pressure is too large to compress blood vessels during movement to a specific position, which may affect blood supply of a limb and further lead to skin necrosis. After the tightening, a retractable anti-dropping strip 11 is opened and is fixed together with the compression plate through a strap to prevent the brace from rotating and dropping.

As shown in FIG. 2, spring scales outside a display window are divided into three scale lines, from top to bottom, a third scale line, a second scale line and a first scale line. When pressure inside the brace is large and compression deformation of the spring is serious, a display bar points to a first scale line in the spring position display window. However, when the pressure inside the brace is not large and the compression deformation of the spring is less, the display bar points to a third scale line or a second scale line in the spring position display window. For example, when the pressure in a finger tendon sheath brace is greater than 100 mmHg, the spring display bar points to the first scale line in the spring position display window. When the pressure in the finger tendon sheath brace is greater than or equal to 40 mmHg and less than 100 mmHg, the spring display bar points to the second scale line in the spring position display window. When the pressure in the finger tendon sheath brace is less than 40 mmHg, the spring display bar points to the third scale line in the spring position display window.

Modification of Embodiment 1

Figure 3:
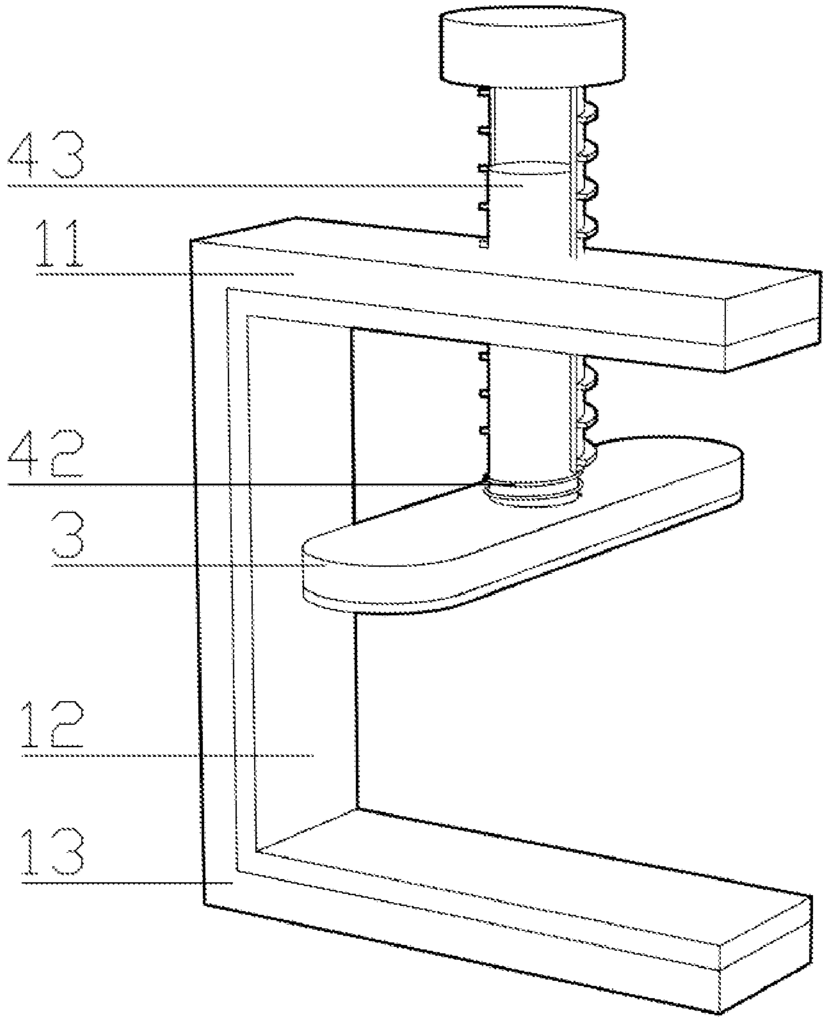
FIG. 3 is a side view of a finger tendon sheath brace according to one embodiment.

A modification of embodiment 1 is shown in FIG. 3. A brace fixing plate is in a shape of a C-shaped opening, including an upper arm, a middle arm and a lower arm. The upper arm and the lower arm are connected by a vertical middle arm. A spring is located at one end of an inner sleeve near a finger, and the end is connected with a compression plate.

Embodiment 2

Figure 5:
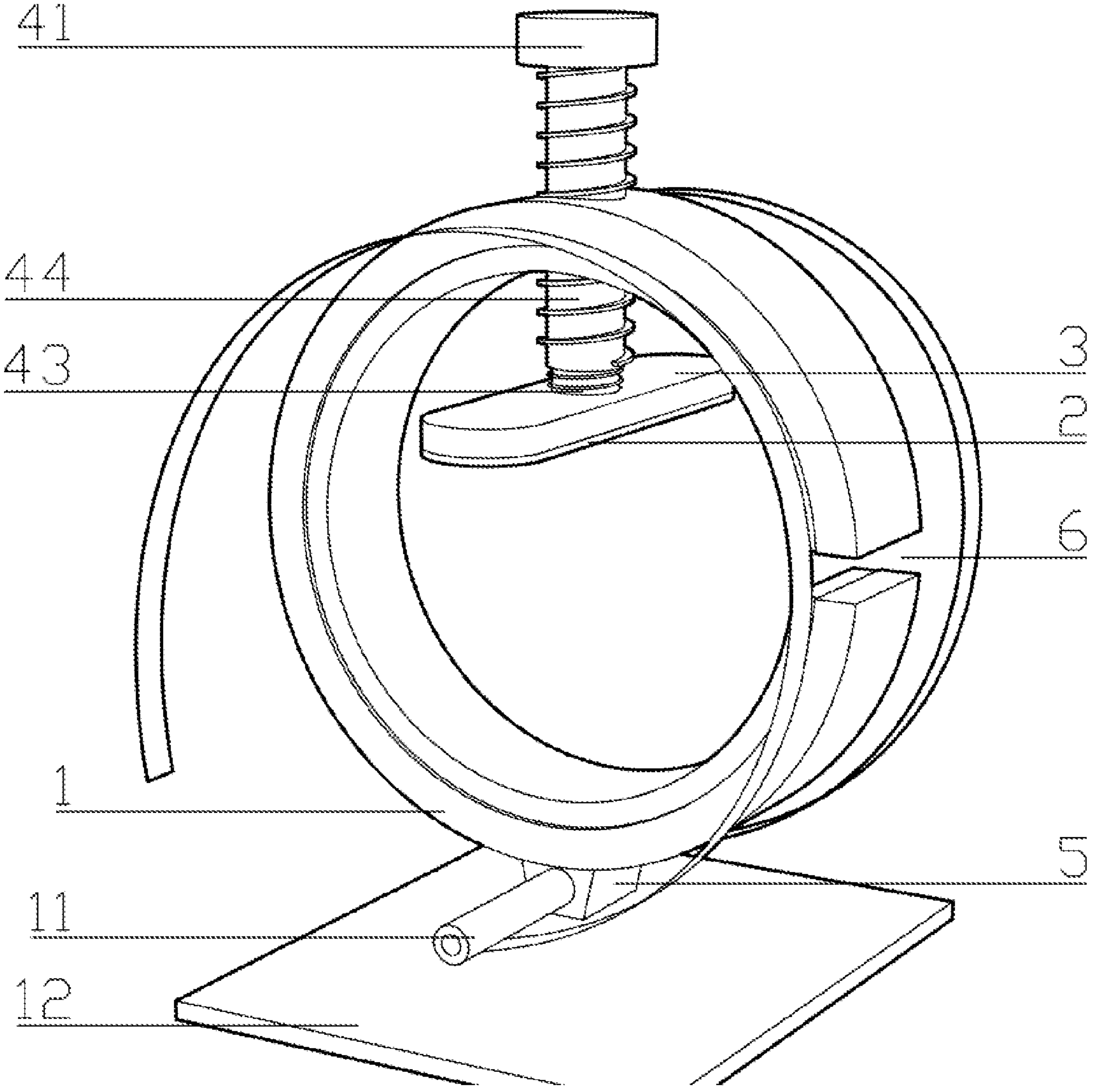
FIG. 5 is a side view of an outer surface of a compression screw according to another embodiment.

Another embodiment of the present application is shown in FIG. 4 and FIG. 5. A brace fixing plate is O-shaped, and includes a notch on a side for a finger to extend in. An outer sleeve is in threaded connection with a compression screw through threads distributed on the outer sleeve. A spring is located between the outer sleeve and an inner sleeve, and at one end of the inner sleeve away from the finger. The finger is put between a compression plate and a brace fixing plate 1, and a compression screw 41 is tighten to a moderate tightness to complete fixation of finger tendon sheath. It is best to make a spring display bar 45 at a low scale during tightening, so as to allow tendon to slide in the tendon sheath, and meanwhile to avoid that soft tissue pressure is too large to compress blood vessels during movement to a specific position, which may affect blood supply of a limb and further lead to skin necrosis. After the tightening, a retractable anti-dropping strip 11 is opened and is fixed together with the compression plate through a strap to prevent the brace from rotating and dropping.

Modification of Embodiment 2

A modification of embodiment 2 is shown in FIG. 5. A brace fixing plate is 0-shaped, and includes a notch on a side for a finger to extend in. A spring is located at one end of an inner sleeve near the finger, and the end is connected with a compression plate.

Embodiment 3

When multiple segments of tendon sheath of a single finger are injured and multiple braces are required for fixation, multiple braces according to the application are connected to form a kit. As shown in FIG. 5, the kit may be connected by installing multiple link rods 12. Installation of hinges depends on rotation and movement of fingers, and rotation centers of interphalangeal joints, that is, transverse stripes of the interphalangeal joints on ventral sides of fingers, should be considered.

It should be noted that in this application, relational terms such as first and second are only used to distinguish one entity or operation from another entity or operation, without necessarily requiring or implying any such actual relationship or order between these entities or operations. Moreover, terms "comprising", "including" or any other variation thereof are intended to cover non-exclusive inclusion, so that a process, a method, an article or equipment including a series of elements includes not only those elements, but also other elements not explicitly listed or elements inherent to such process, such method, such article or such equipment. Without more restrictions, an element defined by a phrase "including one" does not exclude that there are other identical elements in the process, the method, the article or the equipment including the element. In this application, if it is mentioned that an act is executed according to a certain element, it means that the act is executed at least according to that element, which includes two cases: the act is executed only according to that element, and the act is executed according to that element and other elements. Expressions such as multiple, multiple times and multiple kinds include 2, 2 times, and 2 kinds and more than 2, more than 2 times or more than 2 kinds.

This specification includes combinations of various embodiments described herein. A single reference to "one embodiment" or a specific embodiment, etc., does not necessarily refer to a same embodiment. However, these embodiments are not mutually exclusive unless indicated as mutually exclusive or it is clear to those skilled in the art that they are mutually exclusive. It should be noted that unless the context clearly indicates or requires otherwise, a word "or" is used in a non-exclusive sense in this specification.

All documents mentioned in this application are considered to be included in disclosure of this application as a whole, so that they may be used as a basis for revision when necessary. In addition, it should be understood that based on the above disclosure of this application, those skilled in the art may make various changes or modifications to this application, and these equivalent forms also fall within a scope of protection claimed in this application.

What is claimed is:

1. A finger tendon sheath brace capable of adjusting fixing pressure, comprising a brace fixing plate, a compression screw, a compression plate, an adjustable pressure push rod and a spring; wherein the brace fixing plate is configured as a fixing structure for accommodating a finger to extend in the finger tendon sheath brace, and is provided with a threaded opening in a center of the brace fixing plate in a vertical direction perpendicular to the finger;

the compression screw is embedded in the threaded opening of the brace fixing plate through threads to make an end of the compression screw higher than the brace fixing plate and a head end of the compression screw pass through the brace fixing plate and enter a cavity for accommodating the finger;

the compression plate is connected with a head end of an adjustable pressure push rod inner sleeve; and the spring is arranged in the compression screw and used for adjusting a pressure applied on the compression plate by the compression screw, so as to fix tendon sheath;

wherein a lower part of the compression screw is connected with a sleeve structure, the sleeve structure has a layered structure with inner and outer layers and comprises the adjustable pressure push rod inner sleeve and an adjustable pressure push rod outer sleeve;

external threads are arranged on the adjustable pressure push rod outer sleeve for matching with the head end of the compression screw; and the adjustable pressure push rod inner sleeve is sleeved inside the adjustable pressure push rod outer sleeve and vertically displaces relative to the adjustable pressure push rod outer sleeve through the spring;

wherein the spring is arranged at an end of the adjustable pressure push rod inner sleeve close to the finger or at an end away from the finger in the vertical direction.

2. The finger tendon sheath brace according to claim 1, wherein a shape of the brace fixing plate is selected from a group consisting of an O-ring, a rectangular ring, and a C-shaped semi-ring with one side open.

3. The finger tendon sheath brace according to claim 1, wherein the compression plate has a narrow strip structure.

4. The finger tendon sheath brace according to claim 1, wherein the compression plate is connected with the adjustable pressure push rod inner sleeve.

5. The finger tendon sheath brace according to claim 1, wherein a skin-friendly soft sponge is attached to one end of the compression plate in direct contact with the finger, and an inner surface of the brace fixing plate is covered with the skin-friendly soft sponge.

6. The finger tendon sheath brace according to claim 1, wherein when the spring is located at the end of the adjustable pressure push rod inner sleeve away from the finger, the adjustable pressure push rod outer sleeve is provided with a transparent spring position display window at a corresponding position of the spring, and a spring display bar is marked on the spring and moves up and down in the spring position display window according to a position of the spring; and an outer side of the spring position display window is provided with scales indicating pressure values of the spring.

7. The finger tendon sheath brace according to claim 6, wherein pressure states inside the finger tendon sheath brace are marked with three scale lines;

when pressure in the finger tendon sheath is greater than 100 mmHg, the spring display bar corresponds to a first scale line in the spring position display window;

when the pressure in the finger tendon sheath is greater than or equal to 40 mmHg and less than 100 mmHg, the spring display bar corresponds to a second scale line in the spring position display window of the tendon sheath brace; and when the pressure in the finger tendon sheath is less than 40 mmHg, the spring display bar corresponds to a third scale line in the spring position display window of the tendon sheath brace.

8. A kit of a finger tendon sheath brace, comprising a plurality of finger tendon sheath braces according to claim 1, and further comprising link blocks, and retractable anti-dropping strips; wherein the kit is configured to provide tendon sheath fixation for a plurality of finger injuries; and the link blocks connect the multiple finger tendon sheath braces in parallel through link rods.

* * * * *